US012663404B2

(12) United States Patent
Satoh et al.

(10) Patent No.: US 12,663,404 B2
(45) Date of Patent: Jun. 23, 2026

(54) POLYMER ANALYSIS APPARATUS AND METHOD

(71) Applicant: JEOL Ltd., Tokyo (JP)

(72) Inventors: Takaya Satoh, Tokyo (JP); Masahiro Hashimoto, Tokyo (JP); Haruo Iwabuchi, Tokyo (JP)

(73) Assignee: JEOL Ltd., Tokyo (JP)

( * ) Notice: Subject to any disclaimer, the term of this patent is extended or adjusted under 35 U.S.C. 154(b) by 412 days.

(21) Appl. No.: 18/374,084

(22) Filed: Sep. 28, 2023

(65) Prior Publication Data

US 2024/0110897 A1      Apr. 4, 2024

(30) Foreign Application Priority Data

Sep. 29, 2022    (JP) ................................. 2022-156709

(51) Int. Cl.
*G01N 30/72*        (2006.01)
*G01N 30/86*        (2006.01)
*G16C 20/20*        (2019.01)
*G16C 20/80*        (2019.01)

(52) U.S. Cl.
CPC ......... *G01N 30/72* (2013.01); *G01N 30/8631* (2013.01); *G16C 20/20* (2019.02); *G16C 20/80* (2019.02)

(58) Field of Classification Search
CPC .... G01N 30/72; G01N 30/8631; G16C 20/20; G16C 20/80
See application file for complete search history.

(56) References Cited

U.S. PATENT DOCUMENTS

| | | | | |
|---|---|---|---|---|
| 2011/0121172 A1* | 5/2011 | Savitski | ................. | G16C 20/20 |
| | | | | 250/288 |
| 2018/0019110 A1 | 1/2018 | Kubo | | |
| 2020/0312641 A1* | 10/2020 | Byer | ................... | H01J 49/0036 |
| 2020/0328069 A1 | 10/2020 | Boskamp | | |
| 2021/0065849 A1* | 3/2021 | Uematsu | ................ | G16C 20/20 |
| 2022/0122825 A1 | 4/2022 | Satoh | | |

FOREIGN PATENT DOCUMENTS

| | | |
|---|---|---|
| JP | 201790228 A | 5/2017 |
| JP | 20208314 A | 1/2020 |

(Continued)

OTHER PUBLICATIONS

MALDI_TOFMS Application: Estimation of Elemental Composition of End Group of Polymer Using Accurate Mass, Jeol Ltd, 2021, ms Tips No. 357, English-language excerpt included.

(Continued)

*Primary Examiner* — Ricky Go
(74) *Attorney, Agent, or Firm* — The Webb Law Firm

(57) ABSTRACT

A second polymer is prepared through derivatization of a first polymer. Kendrick Mass Defect (KMD) analysis is applied on a mass spectrum of the second polymer, to thereby produce a plot. Meanwhile, a plurality of mass candidates for a non-primary-chain segment are calculated based on a mass spectrum of the first polymer. The KMD analysis is applied on the plurality of mass candidates, to thereby produce reference images. A mass of the non-primary-chain segment is identified through matching of two KMD analysis results.

11 Claims, 12 Drawing Sheets

(56) References Cited

FOREIGN PATENT DOCUMENTS

| | | |
|---|---|---|
| JP | 6668188 B2 | 3/2020 |
| JP | 202267719 A | 5/2022 |

OTHER PUBLICATIONS

Office Action issued in JP2022156709 on Oct. 1, 2024.

Extended European Search Report issued in EP23198868.4 on Feb. 22, 2024.

Sato et al., Structural Characterization of Plymers by MALDI Spiral-TOF Mass Spectrometry Combined with Kendrick Mass Defect Anaylsis, Journal of the American Society for Mass Spectrometry, vol. 25, 2014, pp. 1346-1355.

Ishitsuka et al., An arsenal of tools based on Kendrick mass defects to process congested electrospray ionization high-resolution mass spectra of polymers with multiple charging, Rapid Communications in Mass Spectrometry, vol. 34, 2020, pp. 1-13.

Nakamura et al., Molecular Characterization of High Molecular Weight Polyesters by Matrix-Assisted Laser Desorption/Ionization High-Resolution Time-of-Flight Mass Spectrometry Combined with On-plate Alkaline Degradation and Mass Defect Analysis, Journal of the American Society for Mass Spectrometry, vol. 30, 2019, pp. 355-367.

Fouquet et al., On the Kendrick Mass Defect Plots of Multiply Charged Polymer Ions: Splits, Misalignments, and How to Correct Them, Journal of the American Society for Mass Spectrometry, vol. 29, 2018, pp. 1611-1626.

Dimzon et al., High Resolution Mass Spectrometry of Polyflurinated Polyether-Based Formulation, Journal of the American Society for Mass Spectrometry, vol. 27, 2016, pp. 309-318.

Poyer et al., Convenient Graphical Visualization of Messages Encoded in Sequence-Defined Synthetic Polymers Using Kendrick Mass Defect Analysis of their MS/MS Data, Macromolecular Chemistry and Physics, vol. 219, 2018, pp. 1-9.

Fouquet et al., First Gut Instincts Are Always Right: The Resolution Required for a Mass Defect Analysis of Polymer Ions Can Be as Low as Oligomeric, Analytical Chemistry, vol. 90, 2018, pp. 2404-2408.

Fouquet, Thierry N.J., The Kendrick analysis for polymer mass spectrometry, Journal of Mass Spectrometry, vol. 54, 2019, pp. 933-947.

Montaudo et al., Characterization of Polymers by Matrix-Assisted Laser Desorption Ionization-Time of Flight Mass Spectrometry, End Group Determination and Molecular Weight Estimates in Poly(ethylene glycols), Mazromolecules, vol. 28, No. 13, 1995, pp. 4562-4569.

Yalcin et al., Structural Analysis of Polymer End Groups by Electrospray Ionization High-Energy Collision-Induced Dissociation Tandem Mass Spectrometry, Analytical Chemistry, vol. 72, No. 16, 2000, pp. 3847-3852.

Duez et al., One Step Further in the Characterization of Synthetic Polymers by lon Mobility Mass Spectrometry: Evaluating the Contribution of Eng-groups, Polymers, vol. 11, No. 688, 2019, pp. 1-13.

* cited by examiner

| Index | $ME_i$ | DEGREE OF POLYMERIZATION |
|-------|--------|--------------------------|
| #1 | $ME_1$ | $N_1$ |
| #2 | $ME_2$ | $N_2 (=N_1-1)$ |
| #3 | $ME_3$ | $N_3 (=N_1-2)$ |
| ... | ... | ... |

| Index | $ME_{ij}$ | DEGREE OF POLYMERIZATION | | |
|---|---|---|---|---|
| #11 | $ME_{11}$ | $N_{11}$ | | |
| #12 | $ME_{12}$ | $N_{12}(=N_{11}-1)$ | | 134 |
| #13 | $ME_{13}$ | $N_{13}(=N_{11}-2)$ | | |
| #21 | $ME_{21}$ | $N_{21}$ | | |
| #22 | $ME_{22}$ | $N_{22}(=N_{21}-1)$ | | 136 |
| #23 | $ME_{23}$ | $N_{23}(=N_{21}-2)$ | | |

START

PREPARE SAMPLE B FROM SAMPLE A — S20

MASS SPECTROMETRY OF SAMPLES A, B — S22

PRODUCE TWO PLOTS FOR SAMPLE A — S24

IDENTIFY ANALYSIS TARGET SERIES — S26

CREATE MASS CANDIDATE LIST — S28

PRODUCE TWO PLOTS FOR SAMPLE B — S30

DISPLAY TWO PLOTS AND TWO REFERENCE IMAGES — S32

IDENTIFY MASS — S34

ESTIMATE COMPOSITION OF END GROUP — S36

END

POLYMER ANALYSIS APPARATUS AND METHOD

CROSS REFERENCE TO RELATED APPLICATION

This application claims priority to Japanese Patent Application No. 2022-156709 filed Sep. 29, 2022, the disclosure of which is hereby incorporated by reference in its entirety.

BACKGROUND OF THE DISCLOSURE

Field of the Disclosure

The present disclosure relates to an apparatus and a method for analyzing a polymer, and in particular to a technique for analyzing a mass of an end group or the like.

Description of Related Art

A polymer is formed from a plurality of molecules having various degrees of polymerization (hereinafter, also referred to as a "polymer molecule"). Each individual polymer molecule is formed from a primary chain segment and a segment (portion) other than the primary chain (hereinafter also referred to as a "non-primary-chain segment").

The primary chain segment has a structure in which a plurality of repeating units are connected. The number of the repeating units forming the primary chain segment is the degree of polymerization. The non-primary-chain segment includes two end groups connected at respective ends of the primary chain segment. In the present disclosure, these two end groups will be also simply referred to as an "end group". In some cases, the non-primary-chain segment may include one or a plurality of adduct ions. For example, when a polymer is cationized using a cationization agent, one or a plurality of adduct ions are attached to the primary chain segment of each polymer molecule. In the present disclosure, the one or a plurality of adduct ions included in the non-primary-chain segment will be also simply referred to as an "adduct ion".

A mass spectrum acquired through mass spectrometry of a polymer includes a plurality of peaks (mass peaks) corresponding to a plurality of polymer molecules having different degrees of polymerization. The plurality of polymer molecules having different degrees of polymerization may also be called a polymer series. In the mass spectrum of the polymer, a peak interval corresponds to a mass of the repeating unit; that is, a mass of a monomer molecule. In general, it is easy to predict presence or absence of the adduct ion, or to predict the mass of the adduct ion. On the other hand, it is very difficult to directly estimate a mass of the end group from the mass spectrum of the polymer.

As a method of analyzing polymers, Kendrick Mass Defect analysis (KMD analysis) is known (for example, refer to Document 1 described below). In the KMD analysis, using a ratio between an accurate mass of the repeating unit and a nominal mass of the repeating unit, Kendrick Mass Defect (KMD) is determined as a feature quantity which does not depend on the mass of the repeating unit (which can also be said to be the mass of the primary chain segment), and which depends on the mass of the non-primary-chain segment.

In general, a chemical property of the polymer is significantly affected by the end group included in each polymer molecule. Therefore, in the polymer analysis, it is important to identify a composition of the end group. In the KMD analysis of the related art, however, it is not possible to identify the mass of the non-primary-chain segment including the end group.

Document 2 described below describes a technique for estimating a composition of an end group in a polymer. However, Document 2 does not describe estimation of a composition of an end group using two polymers which are in a special relationship.

RELATED ART DOCUMENTS

Document 1: JP 2020-008314 A
Document 2: "Estimation of Elemental Composition of End Group of Polymer Using Accurate Mass" (Applications note MS:MSTips No. 357), 2021, JEOL Ltd., Available on the Internet (Searched on Sep. 27, 2022) <URL: https://www.jeol.co.jp/applications/detail/2160.html>

An advantage of the present disclosure lies in identifying a mass of a non-primary-chain segment of a polymer. Alternatively, an advantage of the present disclosure lies in provision of information for identifying a mass of a non-primary-chain segment in a polymer.

SUMMARY OF THE DISCLOSURE

According to one aspect of the present disclosure, there is provided a polymer analysis apparatus comprising: a processor configured to process a first mass spectrum of a first polymer, and a second mass spectrum of a second polymer having a non-primary-chain segment which is identical to a non-primary-chain segment of the first polymer, wherein the processor is configured to: calculate at least one mass candidate for the non-primary-chain segment based on a first polymer molecule mass and a first repeating unit mass identified from the first mass spectrum; apply Kendrick Mass Defect (KMD) analysis on the at least one mass candidate using the first repeating unit mass, to thereby produce a first KMD analysis result; apply KMD analysis on the second mass spectrum using a second repeating unit mass identified from the second mass spectrum, to thereby produce a second KMD analysis result; and produce an image for identifying a mass of the non-primary-chain segment or judge the mass of the non-primary-chain segment based on the first KMD analysis result and the second KMD analysis result.

According to another aspect of the present disclosure, there is provided a method of analyzing a polymer, the method comprising: calculating, based on a first polymer molecule mass and a first repeating unit mass identified from a first mass spectrum of a first polymer, at least one mass candidate for a non-primary-chain segment of the first polymer; applying Kendrick Mass Defect (KMD) analysis on the at least one mass candidate using the first repeating unit mass, to thereby produce a first KMD analysis result; applying KMD analysis on a second mass spectrum of a second polymer having a non-primary-chain segment which is identical to the non-primary-chain segment of the first polymer, using a second repeating unit mass identified from the second mass spectrum, to thereby produce a second KMD analysis result; and producing an image for identifying a mass of the non-primary-chain segment or judging the mass of the non-primary-chain segment based on the first KMD analysis result and the second KMD analysis result.

BRIEF DESCRIPTION OF THE DRAWINGS

Embodiment(s) of the present disclosure will be described based on the following figures, wherein:

FIG. 11 is a diagram showing a second example of the mass candidate list;

DESCRIPTION OF NON-LIMITING EMBODIMENTS OF THE DISCLOSURE

Figure 1:
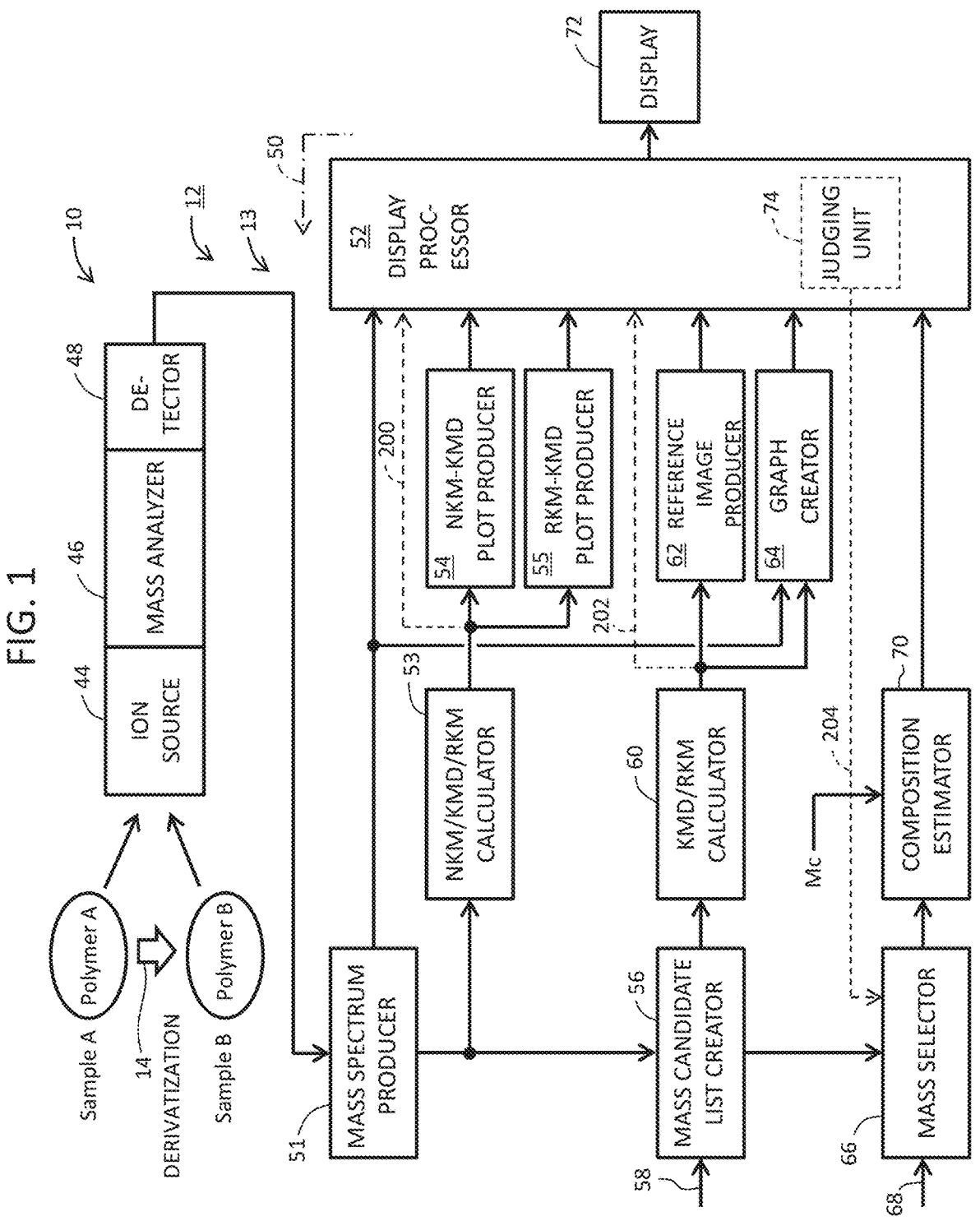
FIG. 1 is a block diagram showing a polymer analysis system according to an embodiment of the present disclosure.

An embodiment of the present disclosure will now be described with reference to the drawings.

(1) Overview of Embodiment

A polymer analysis apparatus according to an embodiment of the present disclosure comprises a processor configured to process a first mass spectrum of a first polymer, and a second mass spectrum of a second polymer having a non-primary-chain segment which is identical to a non-primary-chain segment of the first polymer. The processor is configured to: calculate at least one mass candidate for the non-primary-chain segment based on a first polymer molecule mass and a first repeating unit mass identified from the first mass spectrum; and apply Kendrick Mass Defect (KMD) analysis on the at least one mass candidate using the first repeating unit mass, to thereby produce a first KMD analysis result. The processor is further configured to apply KMD analysis on the second mass spectrum using a second repeating unit mass identified from the second mass spectrum, to thereby produce a second KMD analysis result. The processor is further configured to produce an image for identifying a mass of the non-primary-chain segment or judge the mass of the non-primary-chain segment based on the first KMD analysis result and the second KMD analysis result.

According to the structure described above, by taking advantage of a special relationship between the first polymer and the second polymer, the mass of the non-primary-chain segment common to these polymers can be identified. More specifically, by applying the KMD analysis on the mass candidate calculated from the first mass spectrum, a feature quantity which does not depend on the first repeated unit mass and which depends on the mass of the non-primary-chain segment is determined. On the other hand, by applying the KMD analysis on the second mass spectrum, a feature quantity which does not depend on the second repeating unit mass and which depends on the mass of the non-primary-chain segment is determined. Through matching of these feature quantities, the mass of the non-primary-chain segment common to the first polymer and the second polymer can be identified.

When the non-primary-chain segment does not include the adduct ion, the mass of the non-primary-chain segment can be assumed to be equal to the mass of the end group (normally, a total mass of two end groups). When the non-primary-chain segment includes the adduct ion, the mass of the end group can be identified by subtracting the mass of the adduct ion from the mass of the non-primary-chain segment. A composition of the end group can then be estimated from the mass of the end group.

In an embodiment of the present disclosure, the processor is further configured to: produce a plot representing the second KMD analysis result; and produce a reference image representing the first KMD analysis result and which is to be added to the plot. The image for identifying the mass of the non-primary-chain segment, described above, includes the plot and the reference image. By comparing the contents of the plot with the reference image, it is possible to narrow down the mass of the non-primary-chain segment. The mass of the non-primary-chain segment may be judged by a user, or automatically. Alternatively, the mass of the non-primary-chain segment may be automatically judged through direct matching of the first KMD analysis result and the second KMD analysis result. The plot corresponds to a map or a chart.

In an embodiment of the present disclosure, the plot includes at least one of an NKM-KMD plot having a Nominal Kendrick Mass (NKM) axis and a KMD axis, or an RKM-KMD plot having a Remainder of Kendrick Mass (RKM) axis and the KMD axis. Both the NKM-KMD plot and the RKM-KMD plot have the KMD axis. The KMD is a feature quantity that does not depend on the mass of the repeating unit and that depends on the mass of the non-primary-chain segment.

Until now, a plurality of types of KMDs have been proposed. The KMDs are common with each other in that the KMDs do not depend on the mass of the repeating unit and depend on the mass of the non-primary-chain segment. In an embodiment of the present disclosure, an arbitrary KMD may be used. Similarly, until now, a plurality of RKMs have been proposed. The RKMs are common with each other in that the RKMs do not depend on degrees of polymerization. In an embodiment of the present disclosure, an arbitrary RKM may be used.

In an embodiment of the present disclosure, the processor is further configured to calculate a plurality of mass candidates for the non-primary-chain segment. The reference image includes at least one of a first reference image including a plurality of figures representing a plurality of KMDs calculated from the plurality of mass candidates and displayed on the NKM-KMD plot, or a second reference image including a plurality of figures representing a plurality of sets of RKM-KMDs calculated from the plurality of mass candidates and displayed on the RKM-KMD plot.

Alternatively, only one of the NKM-KMD plot and the RKM-KMD plot may be displayed. In this case, a reference image corresponding to the displayed plot is displayed. When both the NKM-KMD plot and the RKM-KMD plot are displayed, the analysis of the polymer can be performed more appropriately. In this case, two reference images corresponding to the two displayed plots are displayed. In an embodiment of the present disclosure, each of the figures in the first reference image has a line-shape form, and each of the figures in the second reference image has a circular form. The line-shape form includes a solid line, a dashed line, an arrow, a band, and the like. The circular form includes a circle, an ellipse, an encircling figure, and the like.

In an embodiment of the present disclosure, the processor is further configured to calculate a plurality of mass candidates by repeating subtraction of the first repeating unit mass from the first polymer molecule mass. In an embodiment of the present disclosure, the processor is further configured to determine, when a remaining mass after subtraction belongs in a mass range that is designated, the remaining mass as a mass candidate. The mass range is designated by the user or automatically according to various conditions.

In an embodiment of the present disclosure, the processor is further configured to repeat calculation of a degree of polymerization along with repetition of the subtraction, to thereby create a list in which a plurality of mass candidates and a plurality of degrees of polymerization corresponding thereto are registered. According to this structure, it becomes possible to take into consideration a plurality of degrees of polymerization in the process of identifying the mass of the non-primary-chain segment from the plurality of mass candidates. The reference image is produced based on the contents of the list.

In an embodiment of the present disclosure, the processor is further configured to calculate a total ionic strength for each calculated KMD based on the second mass spectrum, to thereby create a graph representing a plurality of total ionic strengths corresponding to a plurality of KMDs. According to this structure, the mass of the no-primary-chain segment can be judged while taking into consideration the contents of the graph, and based on a relationship between the plot and the reference image. The graph is, for example, a bar graph.

In an embodiment of the present disclosure, one of the first polymer and the second polymer is a polymer before derivatization, and the other of the first polymer and the second polymer is a polymer after derivatization. According to the derivatization, two polymers which differ only in the primary chain segment (that is, having a common non-primary-chain segment) can be easily prepared.

According to an embodiment of the present disclosure, there is provided a method of analyzing a polymer, the method comprising: a calculation step, a first analysis step, a second analysis step, and a processing step. In the calculation step, based on a first polymer molecule mass and a first repeating unit mass identified from a first mass spectrum of a first polymer, at least one mass candidate for a non-primary-chain segment of the first polymer is calculated. In the first analysis step, Kendrick Mass Defect (KMD) analysis is applied on the at least one mass candidate using the first repeating unit mass, to thereby produce a first KMD analysis result. In the second analysis step, KMD analysis is applied on a second mass spectrum of a second polymer having a non-primary-chain segment which is identical to the non-primary-chain segment of the first polymer, using a second repeating unit mass identified from the second mass spectrum, to thereby produce a second KMD analysis result. In the processing step, an image for identifying a mass of the non-primary-chain segment is produced, or the mass of the non-primary-chain segment is judged based on the first KMD analysis result and the second KMD analysis result.

The first analysis step may be performed before the second analysis step, or the second analysis step may be performed before the first analysis step. Alternatively, the first analysis step and the second analysis step may be performed simultaneously.

The method of analyzing a polymer according to an embodiment of the present disclosure further comprises a preparation step. In the preparation step, one of the first polymer and the second polymer is derivatized, so as to prepare the other of the first polymer and the second polymer.

The method of analyzing the polymer according to an embodiment of the present disclosure can be realized by a function of hardware or a function of software. In the case of the latter, a polymer analysis program is installed in an information processing device via a network or via a transportable recording medium. The information processing device has a non-transitory recording medium which stores the polymer analysis program, and has a processor which executes the polymer analysis program. The processor may be formed from one or a plurality of physical devices. A part of the steps in the polymer analysis method according to an embodiment of the present disclosure may be performed by the user. All or a part of the steps of the polymer analysis method according to an embodiment of the present disclosure may be performed as a service on a network.

(2) Details of Embodiment (2-1) KMD Analysis

First, Kendrick Mass Defect (KMD) analysis will be described. With respect to a mass M of a certain polymer, a Kendrick Mass (KM) is defined as follows.

$$KM = M \times Mri/Mr \qquad \text{(Equation 1)}$$

Here, Mri is a nominal mass (integer mass) of the repeating unit, and Mr is an accurate mass of the repeating unit. The nominal mass is determined from the accurate mass. The accurate mass is a mass including a part after the decimal point.

An integer part of the KM is defined as a Nominal Kendrick Mass (NKM). The Kendrick Mass Defect is defined as a difference between the NKM and the KM, as follows.

$$KMD = NKM - KM \qquad \text{(Equation 2)}$$

On the other hand, the mass M of the polymer can in general be expressed as follows.

$$M = Mr \times n + Me + Mc \qquad \text{(Equation 3)}$$

Here, n represents a degree of polymerization, Me represent a mass of an end group (normally, a total mass of two end groups), and Mc represents a mass of an adduct ion (when a plurality of adduct ions are attached, a total mass of these adduct ions). On the right-hand side of Equation 3, the term (Mr×n) represents a mass of the primary chain segment, and the term (Me+Mc) represents a mass of a segment other than the primary chain segment (non-primary-chain segment).

When the right-hand side of Equation 3 is substituted into M in Equation 1, KM can be expressed as follows.

$$KM = Mri \times n + (Me + Mc)Mri/Mr \qquad \text{(Equation 4)}$$

Because the first term on the right-hand side of Equation 4 is an integer, this term does not contribute to the KMD. In consideration of this, the KMD can be expressed as follows, based on Equations 2 and 4.

$$KMD = \text{Round}\{(Me + Mc)Mri/MR\} - (Me + Mc)Mri/Mr \qquad \text{(Equation 5)}$$

The first term on the right-hand side of Equation 5 is the NKM. Round{ } means a rounding-off function. In Equation 5, the KMD takes a value within a range of −0.5 to +0.5. The KMD does not depend on the degree of polymerization, n. More specifically, the KMD does not depend on the mass of the primary chain segment, and depends on the mass of the non-primary-chain segment. In the KMD analysis, the coefficient (Mri/Mr) is used in order to acquire a feature quantity that does not depend on the mass of the primary chain segment.

For each peak in the mass spectrum of the polymer, a set of NKM-KMD is calculated. With this process, a plurality of sets of NKM-KMDs are acquired corresponding to a plurality of peaks. The plurality of sets of NKM-KMDs are expressed as a plurality of display elements on a two-dimensional coordinate system having an NKM axis and a KMD axis. With this process, a KMD plot (more accurately, an NKM-KMD plot) is produced.

In the KMD plot, a plurality of display elements corresponding to a plurality of peaks created from a certain polymer are arranged in parallel with the horizontal axis and in equal intervals. For example, each display element is a circle, and, in this case, a diameter of each circle is determined according to an area (ionic strength) of each peak. There also is known a KMD which takes a value within a range of 0 to 1.0. Such a KMD may alternatively be used in the embodiment of the present disclosure.

Next, a Remainder of Kendrick Mass (RKM) will be described. A part after the decimal point in a quotient obtained by dividing KM by Mri is RKM. Specifically, RKM is defined as follows.

$$RKM=KM/Mri-\text{Floor}(KM/Mri) \qquad \text{(Equation 6)}$$

Here, Floor( ) represents a truncation function.

When the right-hand side of Equation 4 is substituted into KM in Equation (6), the following Equation (7) can be derived.

$$RKM=(n+(Me+Mc)/Mr)-\text{Floor}(n+(Me+Mc)/Mr) \qquad \text{(Equation 7)}$$

In Equation 7, as n is an integer, n may be disregarded. Thus, RKM may be defined as follows.

$$RKM=(Me+Mc)/Mr-\text{Floor}((Me+Mc)/Mr) \qquad \text{(Equation 8)}$$

In a mass spectrum acquired from a polymer, members of a numerical value set formed from Me, Mc, and Mr calculated from each peak are identical with each other. Therefore, the plurality of RKMs calculated from the plurality of peaks have the same value. RKM takes a value within a range of 0 to 1.0. As another method of calculating RKM, there is known a calculation method in which a remainder caused when NKM is divided by Mri is defined as RKM. In this case, RKM takes a value within a range from 0 to Mri.

In general, the set of RKM-KMD is identified for each peak in the mass spectrum of the polymer. With this process, a plurality of sets of RKM-KMDs are acquired corresponding to a plurality of peaks. The plurality of sets of RKM-KMDs are expressed as a plurality of display elements on a two-dimensional coordinate system having an RKM axis and the KMD axis. Thus, an RKM-KMD plot is produced. In the RKM-KMD plot, a plurality of display elements are displayed at the same position, and an overlap is caused among the plurality of display elements. For example, each display element is a circle, and a diameter of the circle is changed according to the peak area (ionic strength).

(2-2) Polymer Analysis System

FIG. 1 shows a polymer analysis system according to an embodiment of the present disclosure. The polymer analysis system is formed from a mass spectrometer 10 and a polymer analysis apparatus 12. In the embodiment, the mass spectrometer 10 applies mass spectrometry on a sample A and a sample B. The polymer analysis apparatus 12 has a function to identify a mass of a non-primary-chain segment of a polymer. In the embodiment, a mass of a non-primary-chain segment common to two polymers, polymers A and B, is identified based on two analysis results for the two polymers A and B which are in a special relationship.

In the embodiment, the sample A and the sample B are each a mass spectrometry target. The sample A contains the polymer A, and the sample B contains the polymer B. For example, the polymer B is prepared through derivatization of the polymer A (refer to reference numeral 14). Prior to the description of the structure of FIG. 1, the polymer A and polymer B will be described with reference to FIG. 2.

Figure 2:
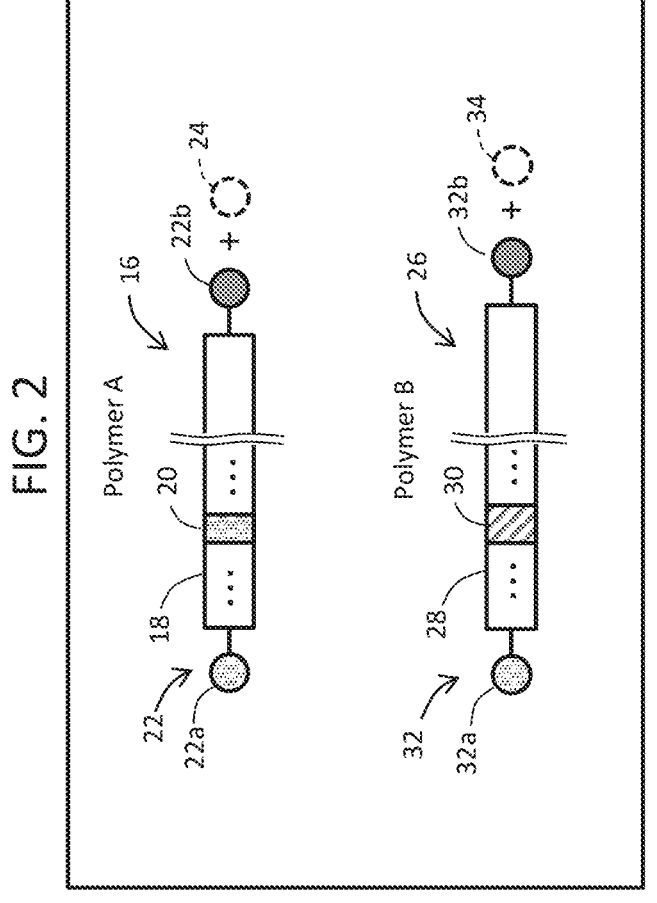
FIG. 2 is a schematic diagram showing structures of polymers A and B.

In an example shown in FIG. 2, each polymer molecule 16 forming the polymer A is formed from a primary chain segment 18, an end group 22, and an adduct ion 24. The primary chain segment 18 has a structure in which a plurality of repeating units 20 are connected. One repeating unit 20 corresponds to a monomer molecule. Specifically, the end group 22 is normally formed from two end groups 22a and 22b bonded to respective ends of the primary chain segment 18. For example, when the polymer A is processed using a cationization agent, the adduct ion 24 is attached to the primary chain segment 18. Normally, a mass of the adduct ion 24 is known. When the adduct ion 24 is attached to the primary chain segment 18, the end group 22 and the adduct ion 24 form the non-primary-chain segment. When the adduct ion 24 is not attached to the primary chain segment 18, the end group 22 forms the non-primary-chain segment.

The polymer B is prepared through derivatization of the polymer A. Alternatively, the polymer B may be prepared through other methods. Similar to each polymer molecule forming the polymer A, each polymer molecule 26 forming the polymer B is formed from a primary chain segment 28, an end group 32, and an adduct ion 34. The primary chain segment 28 has a structure in which a plurality of repeating units 30 are connected. Specifically, the end group 32 is normally formed from two end groups 32a and 32b. When the adduct ion 34 is attached to the primary chain segment 28, the end group 32 and the adduct ion 34 form the non-primary-chain segment. When the adduct ion 34 is not attached to the primary chain segment 28, the end group 32 forms the non-primary-chain segment.

The primary chain segment 18 in the polymer A (repeating unit 20) and the primary chain segment 28 in the polymer B (repeating unit 30) differ from each other. On the other hand, the non-primary-chain segment in the polymer A and the non-primary-chain segment in the polymer B are identical to each other. A special relationship exists between the polymer A and the polymer B. As a method of preparing two polymers in such a special relationship, derivatization may be exemplified. Alternatively, the two polymers in the special relationship may be prepared through other methods.

Figure 3:
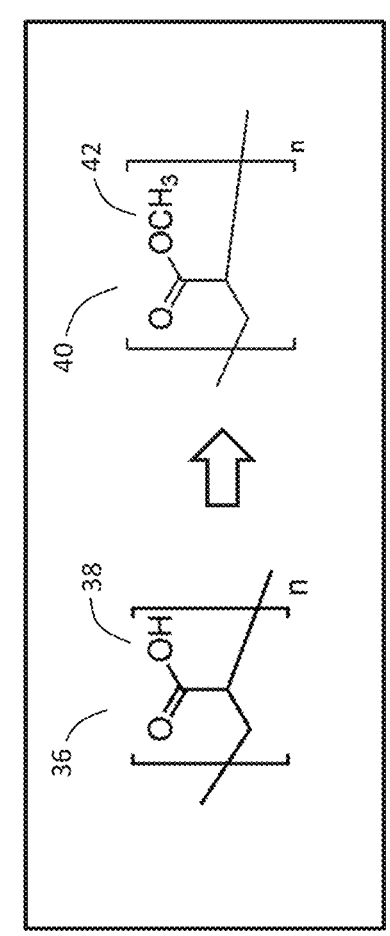
FIG. 3 is a diagram showing derivatization.

FIG. 3 shows an example of the derivatization. Reference numeral 36 shows a repeating unit in the polymer A. The repeating unit 36 includes OH (refer to reference numeral 38). The polymer B is prepared by applying a derivatization reagent on the polymer A. Reference numeral 40 shows a repeating unit in the polymer B. The repeating unit 40 includes $OCH_3$ in place of OH. FIG. 3 shows methylation as an example of the derivatization, but alternatively, other derivatization methods may be employed. A by-product advantage can be obtained through the derivatization, in that an ionization efficiency can be improved.

Referring again to FIG. 1, the mass spectrometer 10 has an ion source 44, a mass analyzer 46, and a detector 48. In the ion source 44, a sample is ionized. As a method of ionization in the ion source 44, there may be exemplified soft ionization methods such as MALDI (Matrix Assisted Laser Desorption/Ionization), ESI (Electrospray ionization), and the like. The mass analyzer 46 is formed from, for example, a time-of-flight type mass analyzer, a Fourier transform-type mass analyzer, or the like. These analyzers can analyze the accurate mass. Ions are detected in the detector 48. An output signal of the detector 48 is sent to the polymer analysis apparatus 12 through a signal processing circuit (not shown).

In the mass spectrometer 10, for example, first, the sample A is measured, and then, the sample B is measured. Alternatively, the order of measurement may be reversed. Alternatively, the two sample may be measured simultaneously, so long as the two spectra acquired from the two samples can be discriminated at a later time.

The polymer analysis apparatus 12 is formed from an information processing device such as a computer. The polymer analysis apparatus 12 has a processor 13 (for example, a CPU) which executes a program. In FIG. 1, a plurality of functions realized by the processor 13 are represented by a plurality of blocks (refer to reference numeral 50). A display 72 is connected to the processor 13, and an inputting device (not shown) is also connected to the processor 13.

A mass spectrum producer 51 produces a mass spectrum based on the output signal from the detector 48. In an embodiment of the present disclosure, the mass spectrum producer 51 consecutively produces a mass spectrum of the sample A and a mass spectrum of the sample B.

For the purpose of simplifying the description, in the following, a configuration is assumed in which the sample A contains only the polymer A and the sample B contains only the polymer B. In this case, the mass spectrum producer 51 produces the mass spectrum of the polymer A as the mass spectrum of the sample A, and produces the mass spectrum of the polymer B as the mass spectrum of the sample B. A case in which the sample A contains a plurality of polymers and the sample B contains a plurality of polymers will be described later with reference to FIGS. 9 and the like.

Data of the mass spectrum of the polymer A and the data of the mass spectrum of the polymer B are sent from the mass spectrum producer 51 via a display processor 52 to the display 72. The mass spectrum of the polymer A and the mass spectrum of the polymer B are displayed on a screen of the display 72.

An NKM/KMD/RKM calculator 53 (hereinafter, simply referred to as a "calculator 53") applies the KMD analysis on each of the mass spectrum of the polymer A and the mass spectrum of the polymer B. More specifically, the calculator 53 executes a calculation of Equation (5) to calculate the KMD (and NKM during this process), and executes a calculation of Equation (8) to calculate the RKM. The accurate mass Mr of the repeating unit is identified from a peak interval in the mass spectrum. The nominal mass Mri of the repeating unit is identified from the accurate mass Mr of the repeating unit. As the KMD analysis result, a feature quantity set formed from the NKM, the KMD, and the RKM is determined for each individual peak included in each mass spectrum.

An NKM-KMD plot producer 54 produces an NKM-KMD plot for each mass spectrum. The NKM-KMD plot has an NKM axis serving as a horizontal axis, and a KMD axis serving as a vertical axis. On a two-dimensional coordinate system defined by the NKM axis and the KMD axis, for each peak, a display element representing a set of NKM-KMD calculated from the peak is mapped, to thereby produce the NKM-KMD plot. For example, each display element is a circle, and a diameter of the circle is determined from an area of each peak.

In an embodiment of the present disclosure, an NKM-KMD plot for the polymer A and an NKM-KMD plot for the polymer B are produced. Data indicating these plots are sent via the display processor 52 to the display 72. The NKM-KMD plot for the polymer A and the NKM-KMD plot for the polymer B are displayed on the screen of the display 72.

An RKM-KMD plot producer 55 produces an RKM-KMD plot for each mass spectrum. The RKM-KMD plot has an RKM axis serving as a horizontal axis, and a KMD axis serving as a vertical axis. On a two-dimensional coordinate system defined by the RKM axis and the KMD axis, for each peak, a display element representing a set of RKM-KMD calculated from the peak is mapped, to thereby produce the RKM-KMD plot. For example, each display element is a circle, and a diameter of the circle is determined from an area of each peak.

In an embodiment of the present disclosure, an RKM-KMD plot for the polymer A and an NKM-KMD plot for the polymer B are produced. Data indicating these plots are sent via the display processor 52 to the display 72. The RKM-KMD plot for the polymer A and the NKM-KMD plot for the polymer B are displayed on the screen of the display 72.

In an embodiment of the present disclosure, in the identification of the mass of the non-primary-chain segment, at least one of the NKM-KMD plot and the RKM-KMD plot is displayed for the polymer B. A reference image to be described below is displayed over the displayed plot. Desirably, both the NKM-KMD plot and the RKM-KMD plot are displayed for the polymer B, and two reference images to be described below are displayed over these two plots.

A mass candidate list creator 56 (hereinafter, simply referred to as a "list creator 56") creates a mass candidate list including a plurality of mass candidates. Specifically, the list creator 56 identifies, based on the mass spectrum of the polymer A, a polymer molecule mass from an arbitrary peak included in the mass spectrum, and identifies a repeating unit mass based on the mass spectrum of the polymer A. Then, the list creator 56 repeatedly executes subtraction of the repeated unit mass from the polymer molecule mass. The list creator 56 judges, when a remaining mass caused after the subtraction belongs in a designated mass range, the remaining mass as a mass candidate. In the identification of the polymer molecule mass, a peak may be designated by the user, or automatically.

The mass range described above is designated by the user in advance (refer to reference numeral 58), or automatically. Alternatively, the mass range may be designated based on an upper limit mass and a lower limit mass expected for the non-primary-chain segment. In an embodiment of the present disclosure, the list creator 56 also repeats calculation of the degree of polymerization during the process of repeating the subtraction of the repeating unit mass from the polymer molecule mass. In the mass candidate list, a plurality of mass candidates and a plurality of degrees of polymerization corresponding thereto are registered. The degree of polymerization is determined from a number of subtractions of the repeating unit mass.

A KMD/RKM calculator 60 (hereinafter, simply referred to as a "calculator 60") applies the KMD analysis on the plurality of mass candidates included in the mass candidate list created from the mass spectrum of the polymer A, to thereby calculate a set of KMD-RKM for each mass candidate. As a result, a plurality of sets of KMD-RKMs are determined corresponding to the plurality of mass candidates. Specifically, the calculator 60 executes the following calculations.

For calculation of the KMD for a mass candidate MEi, the following Equation (9) is executed.

$$KMD=Round\{MEi\times(Mri/Mr)\}-MEi\times(Mri/Mr) \qquad \text{(Equation 9)}$$

Here, Mri represents the nominal mass of the repeating unit in the polymer A, and Mr represents the accurate mass of the repeating unit in the polymer A. Round( ) indicates the rounding-off function.

For calculation of the RKM for the mass candidate MEi, the following Equation (10) is executed.

$$RKM=MEi/Mr-Floor(MEi/Mr) \qquad \text{(Equation 10)}$$

Here, Floor( ) represents a truncation function of a number after the decimal point.

Equation (9) is identical to Equation (5) except for a difference in the mass to be analyzed. Similarly, Equation (10) is identical to Equation (8) except for a difference in the mass to be analyzed.

A reference image producer 62 has a first function to produce a first reference image (first graphic) based on a plurality of KMDs determined from a plurality of mass candidates, and a second function to produce a second reference image (second graphic) based on a plurality of sets of KMD-RKMs determined from a plurality of mass candidates.

The display processor 52 combines the first reference image onto the NKM-KMD plot, and combines the second reference image onto the RKM-KMD plot. On the screen of the display 72, an NKM-KMD plot to which the first reference image is added is displayed, and an RKM-KMD plot to which the second reference image is added is displayed. In an embodiment of the present disclosure, an image including these plots is displayed on the display 72. As will be described later in detail, the mass of the non-primary-chain segment can be identified by comparing the contents of the NKM-KMD plot and the first reference image. Similarly, the mass of the non-primary-chain segment can be identified by comparing the contents of the RKM-KMD plot and the second reference image.

A graph creator 64 creates a graph for assisting identification of the non-primary-chain segment. The graph creator 64 will be described later.

A judging unit 74 may be provided in the display processor 52. The judging unit 74 matches a first KMD analysis result which is output from the calculator 60 and a second KMD analysis result which is output from the calculator 53, to identify the mass of the non-primary-chain segment. In this case, the first KMD analysis result and the second KMD analysis result may be directly matched (refer to reference numerals 200 and 202), or a reference image showing the first KMD analysis result and a plot showing the second KMD analysis result may be matched.

A mass selector 66 selects a particular mass candidate from the plurality of mass candidates as a mass of the non-primary-chain segment. The particular mass candidate may be designated by a user (refer to reference numeral 68). Alternatively, the particular mass candidate may be designated by the judging unit 74 (refer to reference numeral 204).

A composition estimator 70 subtracts, when the non-primary-chain segment includes the adduct ion, a mass Mc of the adduct ion from the mass of the non-primary-chain segment, to identify a mass (accurate mass) of the end group. Then, the composition estimator 70 estimates a composition of the end group based on the mass of the end group. The composition estimator 70 assumes, when the non-primary-chain segment does not include the adduct ion, the mass of the non-primary-chain segment as the mass of the end group, and estimates the composition of the end group based on this mass. A result of the composition estimation is displayed on the display 72.

Figure 4:
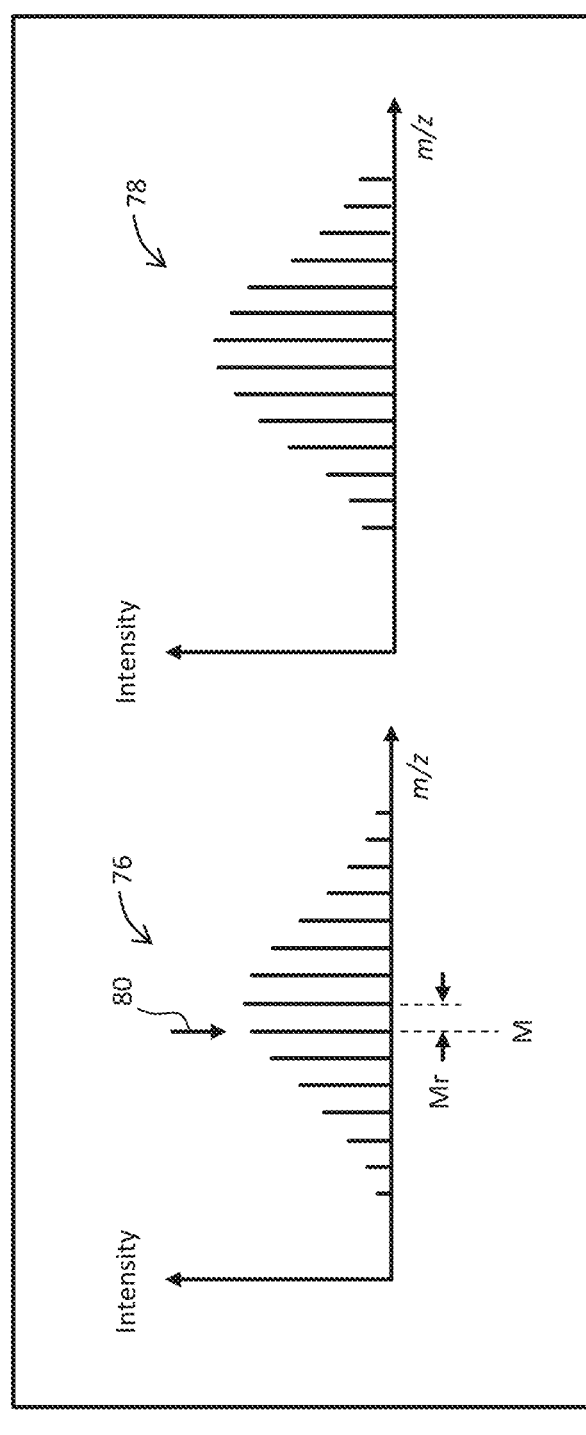
FIG. 4 is a diagram showing examples of a mass spectrum of the polymer A and a mass spectrum of the polymer B.

FIG. 4 shows examples of a mass spectrum 76 acquired from the polymer A and a mass spectrum 78 acquired from the polymer B. In the identification of the mass candidate, a particular peak is designated by the user on the mass spectrum 76 (refer to reference numeral 80). Based on a (m/z) value corresponding to the particular peak, a mass (accurate mass) M of the polymer molecule is identified. A mass (accurate mass) Mr of the repeating unit is identified from an inter-peak size in the mass spectrum 76. Similarly, a mass (accurate mass) of the repeating unit is identified from an inter-peak size in the mass spectrum 78.

Figure 5:
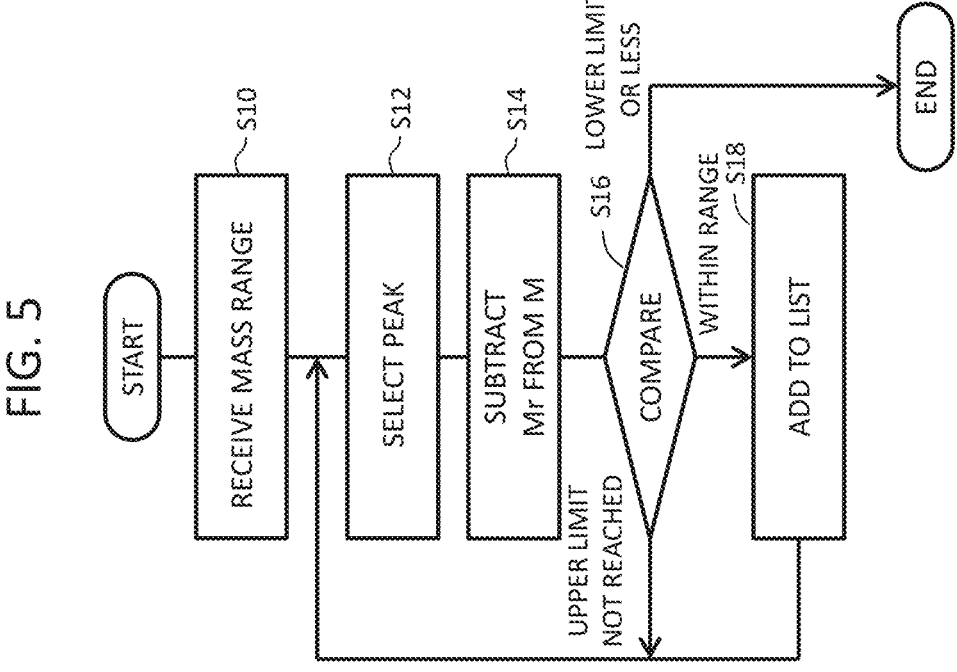
FIG. 5 is a flowchart showing a method of creating a mass candidate list.

FIG. 5 shows an operation of the list creator. In S10, a mass range is received. In this case, an upper limit and a lower limit for the mass of the non-primary-chain segment may be designated by the user. In S12, a particular peak is selected by the user on the mass spectrum of the polymer A. With this process, the mass M of the polymer molecule is identified. At the same time, the mass Mr of the repeating unit for the polymer A is identified.

In S14, a mass Mr of the repeating unit is subtracted from the mass M of the polymer molecule. In S16, the remaining mass caused by the subtraction is compared with the mass range. When the remaining mass has not reached the mass range (when remaining mass >mass range), S12 is again executed. When the remaining mass belongs in the mass range (when remaining mass ⊂ mass range), S18 is executed, the remaining mass is set as a mass candidate, the mass candidate is added to the mass candidate list, and step S12 is again executed. When the remaining mass becomes smaller than the lower limit of the mass range (when remaining mass <mass range), the present procedure is completed.

The subtraction in S14 is repeatedly executed until the completion of the present procedure. That is, the subtraction of the mass Mr of the repeating unit from the mass M of the polymer molecule is repeated. Among the plurality of remaining masses acquired during this procedure, one or a plurality of remaining masses belonging in the mass range is/are judged as one or a plurality of mass candidates. In an embodiment of the present disclosure, the list creator has a function to calculate the degree of polymerization. The degree of polymerization calculated for each mass candidate is also registered in the mass candidate list. The degree of polymerization can be easily identified from a number of repetitions of the subtraction.

Figure 6:
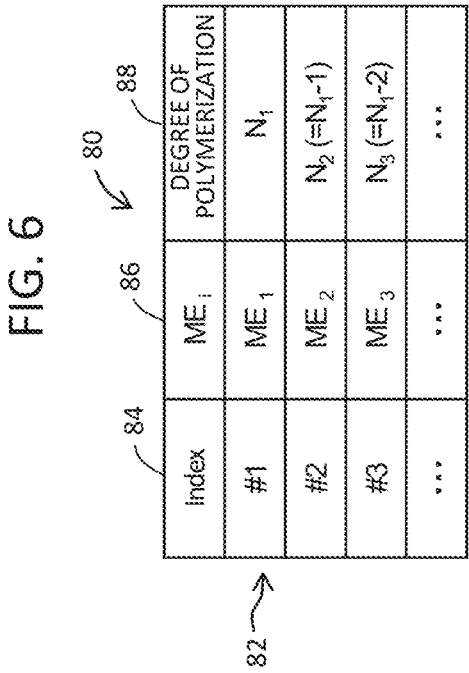
FIG. 6 is a diagram showing a first example of the mass candidate list.

FIG. 6 shows a first example of the mass candidate list. A mass candidate list 80 has a plurality of records 82. One record 82 corresponds to one mass candidate. The record 82 includes information such as an index 84, a mass candidate 86, and a degree of polymerization 88. Due to the repetition of the subtraction process shown in FIG. 5, the degree of polymerization 88 in FIG. 6 is stepwise changed. In the illustrated example, when the index 84 changes by 1, the degree of polymerization 88 is reduced by 1. More specifically, the degree of polymerization 88 changes as $N_1$, $N_2$ ($=N_1-1$), $N_3$ ($=N_1-2$), etc.

Figure 7:
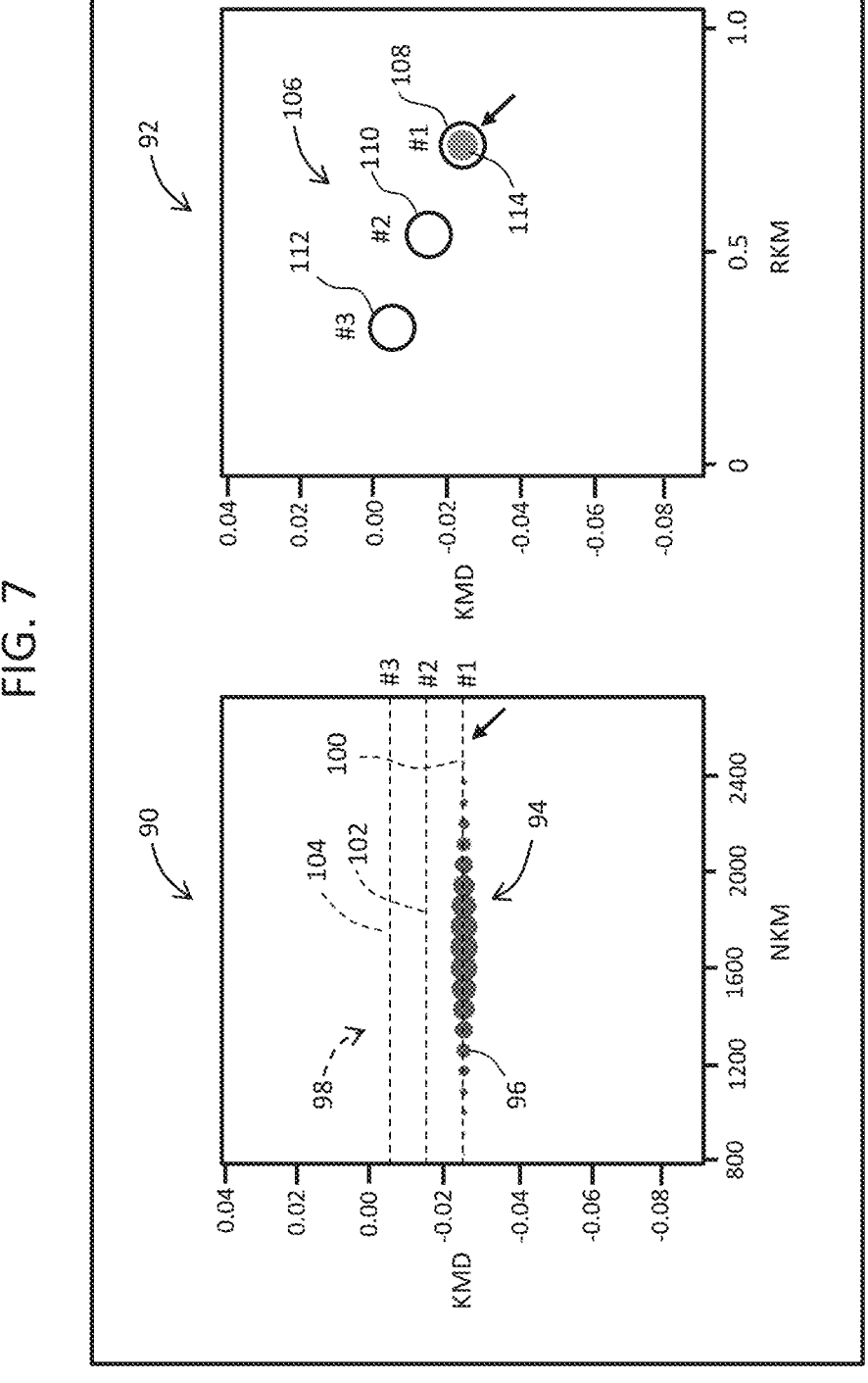
FIG. 7 is a diagram showing a first example of an image including two plots.

FIG. 7 shows an NKM-KMD plot 90 and an RKM-KMD plot 92. Alternatively, a mass spectrum may be displayed along with these plots 90 and 92. In the NKM-KMD plot 90, the horizontal axis represents the NKM axis, and the vertical axis represents the KMD axis. The NKM-KMD plot 90 includes a display element sequence 94 indicating the KMD analysis result for the polymer B. The display element sequence 94 is formed from a plurality of display elements 96 corresponding to a plurality of peaks included in the mass spectrum of the polymer B. Each display element 96 is a circle, and a diameter thereof indicates a peak area. The plurality of display elements forming the display element sequence 94 are arranged parallel to the NKM axis and at equal intervals.

A first reference image 98 produced from the mass spectrum of the polymer A is displayed over the NKM-KMD plot 90. In the illustrated example, the first reference image 98 includes, as a plurality of figures corresponding to a plurality of mass candidates, a plurality of lines 100, 102, and 104. Specifically, the plurality of lines 100, 102, and 104 are displayed at a plurality of vertical positions corresponding to a plurality of KMDs determined from the plurality of mass candidates. An index is displayed near each of the lines 100, 102, and 104. Alternatively, the degree of polymerization may be further displayed near each of the lines 100, 102, and 104.

On the other hand, in the RKM-KMD plot 92, the horizontal axis represents the RKM axis, and the vertical axis represents the KMD axis. The RKM-KMD plot 92 includes a display element group 114 indicating the KMD analysis result for the polymer B. The display element group 114 is formed from a plurality of display elements corresponding to a plurality of peaks included in the mass spectrum of the polymer B. The plurality of display elements are displayed at the same position in a multiplexed manner, and form a single display element in their appearances. Each display element is a circle, and a diameter thereof represents the peak area.

A second reference image 106 produced from the mass spectrum of the polymer A is displayed over the RKM-KMD plot 92. In the illustrated example, the second reference image 106 includes, as a plurality of figures corresponding to a plurality of mass candidates, a plurality of circles 108, 110, and 112. Specifically, the plurality of circles 108, 110, and 112 are displayed at a plurality of coordinates corresponding to the plurality of sets of RKM-KMDs determined from the plurality of mass candidates. The circles 108, 110, and 112 have the same diameter. More specifically, each circle has a size larger than a maximum size of the display element group described above. Alternatively, other encircling figures may be employed. An index is displayed near each of the circles 108, 110, and 112. Alternatively, the degree of polymerization may be further displayed near each of the circles 108, 110, and 112.

In the NKM-KMD plot 90, in regard to a vertical direction, the display element sequence 94 and the line 100 coincide with each other. The coincidence indicates that, among the plurality of mass candidates, a mass candidate corresponding to an index #1 corresponds to the mass of the non-primary-chain segment. In the RKM-KMD plot 92, the display element group 114 belongs in the circle 108. The inclusion relationship indicates that, among the plurality of mass candidates, the mass candidate corresponding to the index #1 corresponds to the mass of the non-primary-chain segment.

In this manner, by comparing the first reference image 98 derived from the polymer A and the NKM-KMD plot 90 derived from the polymer B, it is possible to easily identify the mass of the non-primary-chain segment. Similarly, by comparing the second reference image 106 derived from the polymer A and the RKM-KMD plot 92 derived from the polymer B, it is possible to easily identify the mass of the non-primary-chain segment.

Alternatively, only one of the NKM-KMD plot 90 and the RKM-KMD plot 92 may be displayed. In this case, a reference image corresponding to the displayed plot is displayed. When both the NKM-KMD plot 90 and the RKM-KMD plot 92 are displayed, and both the first reference image 98 and the second reference image 106 are displayed, it is possible to more accurately judge the mass of the non-primary-chain segment. Alternatively, two reference images may be produced from the mass spectrum of the polymer B, and two plots may be produced from the mass spectrum of the polymer A.

Figure 8:
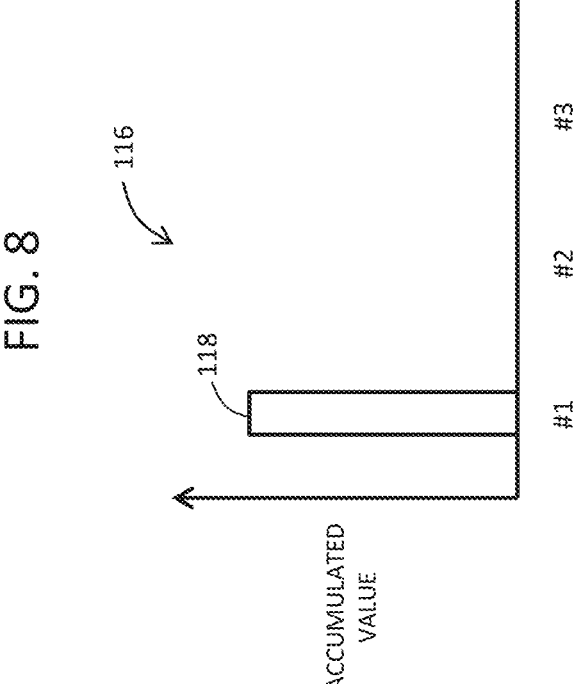
FIG. 8 is a diagram showing a first example of a graph.

FIG. 8 shows a graph 116 serving as an assisting image. The graph 116 is created by calculating, for each of the circles 108, 110, and 112 in the RKM-KMD plot 92 shown in FIG. 7, a total sum of area(s) of one or a plurality of peaks belonging in the circle. In the illustrated example, the graph 116 has a bar 118 corresponding to the index #1. A height of the bar corresponds to a total peak area. In the identification of the mass of the non-primary-chain segment, reference is made to the graph 116.

Figure 9:
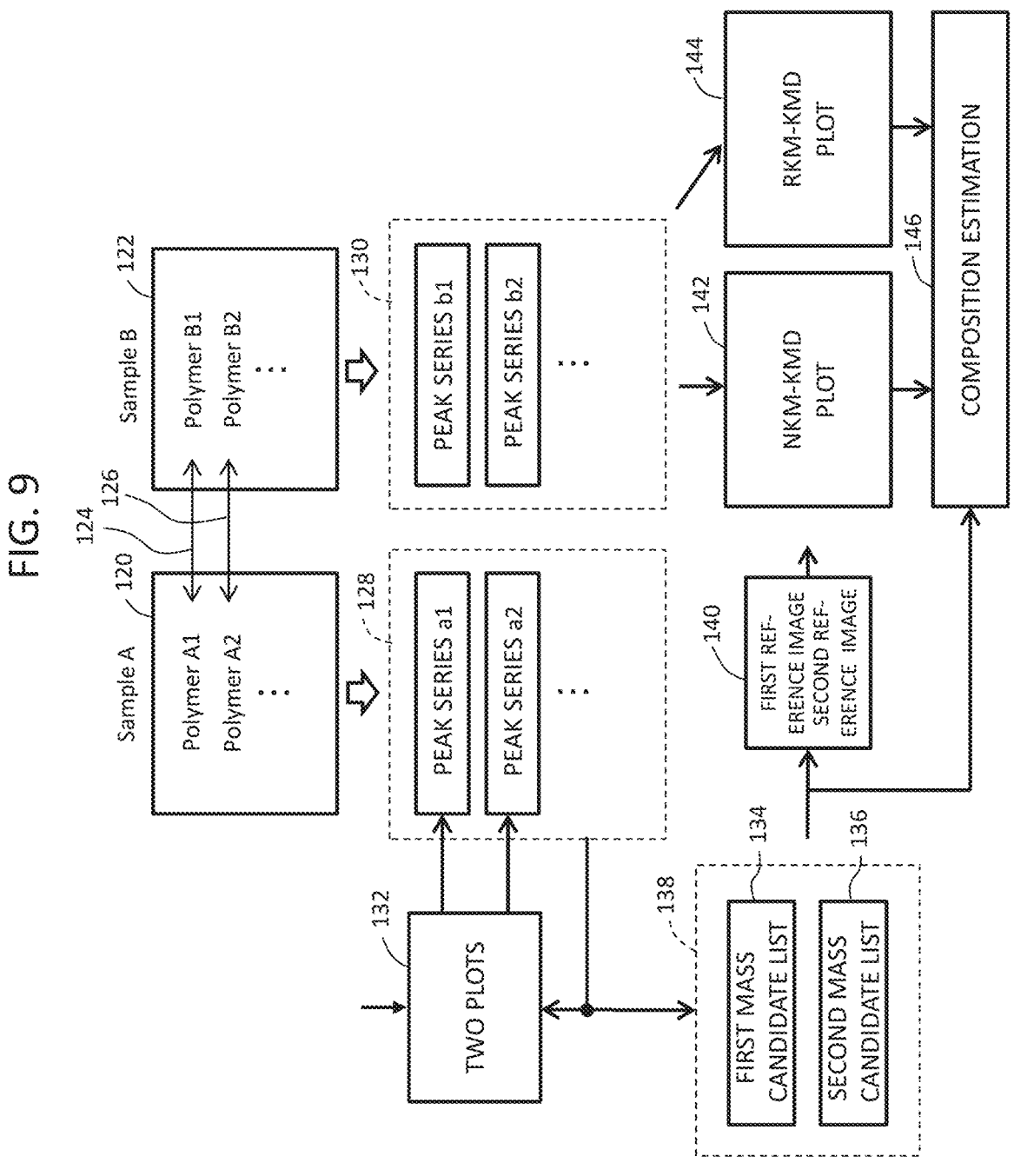
FIG. 9 is a diagram showing an example of polymer analysis.

FIG. 9 shows a more realistic example of the polymer analysis. As shown by reference numeral 120, the sample A contains a plurality of polymers. Of these polymers, a polymer A1 and a polymer A2 are respectively analysis targets. As shown by reference numeral 112, the sample B also contains a plurality of polymers. Of these polymers, a polymer B1 and a polymer B2 are respectively analysis targets. The polymer A1 and the polymer B1 are in the special relationship described above (refer to reference numeral 124). Similarly, the polymer A2 and the polymer B2 are in the special relationship described above (refer to reference numeral 126).

Through mass spectrometry of the sample A, a mass spectrum 128 is acquired. The mass spectrum 128 includes a plurality of peak series corresponding to the plurality of polymers. Of the plurality of the peak series, a peak series a1 is a peak series for the polymer A1, and a peak series a2 is a peak series for the polymer A2. The peak series is formed from a plurality of peaks arranged at equal intervals.

Through mass spectrometry of the sample B, a mass spectrum 130 is acquired. The mass spectrum 130 includes a plurality of peak series corresponding to the plurality of polymers. Of the plurality of the peak series, a peak series b1 is a peak series for the polymer B1, and a peak series b2 is a peak series for the polymer B2.

In order to recognize or extract the individual peak series, the KMD analysis is applied to the mass spectrum, and the NKM-KMD plot and the RKM-KMD plot may be produced based on a result of the KMD analysis (refer to reference numeral 132). When the user designates a display element sequence in the NKM-KMD plot, a particular peak series correlated to the display element sequence is automatically recognized. Similarly, when the user designates a display element group in the RKM-KMD plot, a particular peak series correlated to the display element group is automatically recognized.

Through a subtraction process (refer to FIG. 5) of a mass of a particular peak in the peak series a1, a first mass candidate list 134 is created. Through a subtraction process (refer to FIG. 5) of a mass of a particular peak in the peak series a2, a second mass candidate list 136 is created. Alternatively, the first mass candidate list 134 and the second mass candidate list 136 may be integrated, and a single mass candidate list 138 may be formed. The KMD analysis is applied to a plurality of mass candidates in the first mass candidate list 134, and the first reference image is produced based on a result of the KMD analysis (refer to reference numeral 140). The KMD analysis is applied to a plurality of mass candidates in the second mass candidate list 136, and the second reference image is produced based on a result of the KMD analysis (refer to reference numeral 140).

In the meantime, the KMD analysis is applied to the mass spectrum 130 of the sample B, to produce an NKM-KMD plot 142 and an RKM-KMD plot 144. The first reference image is combined with the NKM-KMD plot 142, and the second reference image is combined with the RKM-KMD plot 144. By the user matching the contents of the NKM-KMD plot 142 and the first reference image, the user can recognize that a particular mass candidate corresponds to a mass of the non-primary-chain segment. Similarly, by the user matching the contents of the RKM-KMD plot 144 and the second reference image, the user can recognize that a particular mass candidate corresponds to a mass of the non-primary-chain segment.

When the mass of the non-primary-chain segment is identified, a mass of the end group is identified from the mass of the non-primary-chain segment while taking into consideration presence or absence of the adduct ion and a mass of the adduct ion. Based on the mass of the end group, the composition of the end group is estimated (refer to reference numeral 146).

Figure 10:
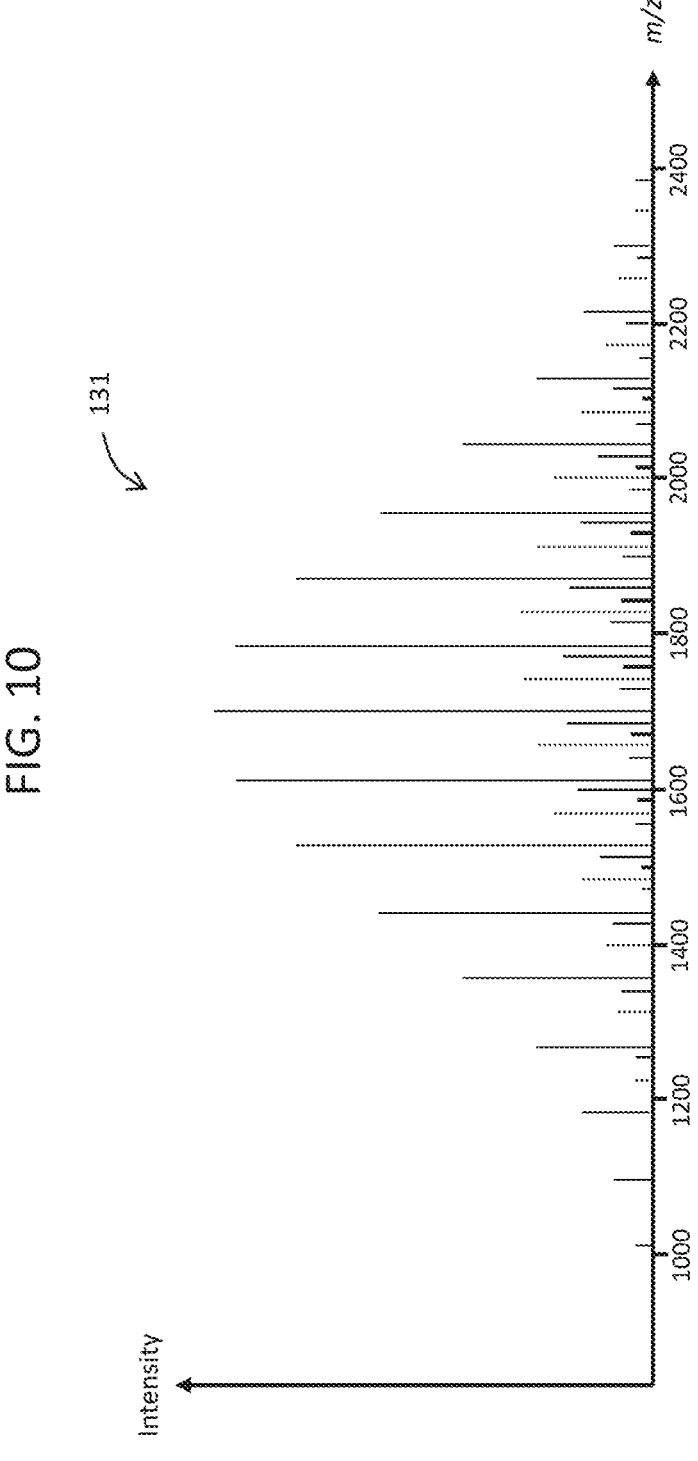
FIG. 10 is a diagram showing another example of a mass spectrum of a polymer.

FIG. 10 shows a mass spectrum 131 as an example. The mass spectrum 131 is the mass spectrum of the sample A or the mass spectrum of the sample B. The mass spectrum 131 includes a plurality of peak series corresponding to a plurality of polymers.

FIG. 11 shows an example of the mass candidate list 138 described above. The mass candidate list 138 is formed from the first mass candidate list 134 created from the peak series a1 described above, and the second mass candidate list 136 created from the peak series a2 described above. Due to the repetition of the subtraction process shown in FIG. 5, in FIG. 11, the degree of polymerization stepwise changes for each peak series (polymer series). In the illustrated example, with a change of the index of 1, the degree of polymerization is reduced by 1. More specifically, in the first mass candidate list 134, the degree of polymerization changes in a manner of $N_{11}$, $N_{12}$ ($=N_{11}-1$), $N_{13}$ ($=N_{11}-2$), etc., and, in the second mass candidate list 136, the degree of polymerization changes in a manner of $N_{21}$, $N_{22}$ ($=N_{21}-1$), $N_{23}$ ($=N_{21}-2$), etc.

Figure 12:
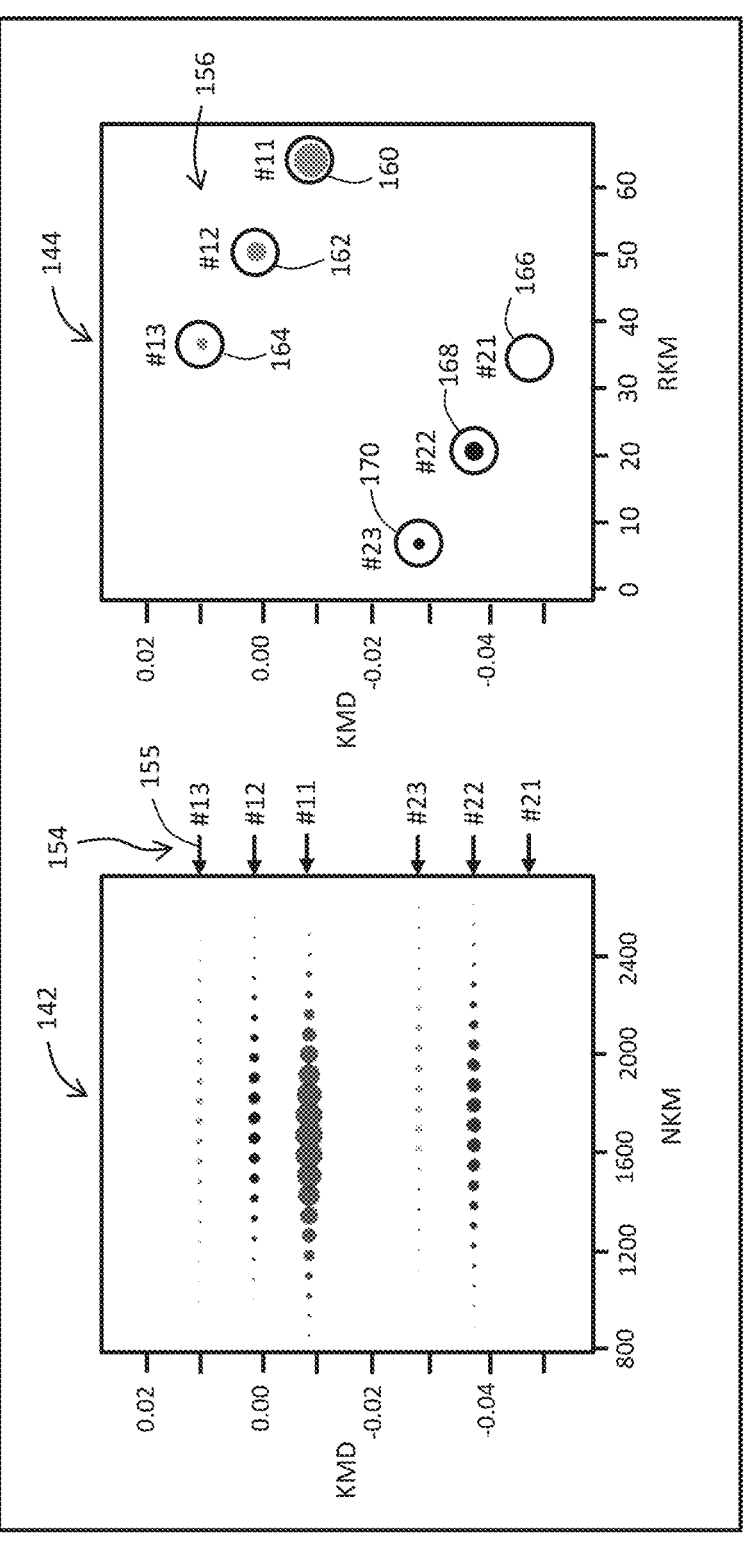
FIG. 12 is a diagram showing a second example of the image including two plots.

FIG. 12 shows examples of the NKM-KMD plot 142 and the RKM-KMD plot 144 produced from the result of the KMD analysis of the mass spectrum of the sample B. FIG. 12 also shows a first reference image 154 and a second reference image 156 produced from the result of the KMD analysis of the plurality of mass candidates in the mass candidate list 138 shown in FIG. 11.

The NKM-KMD plot 142 includes a plurality of display element sequences arranged in a vertical direction. In reality, the NKM-KMD plot 142 may include a larger number of the display element sequences, but FIG. 12 only expresses primary display element sequences. The first reference image 154 has a plurality of arrows 155 corresponding to a plurality of mass candidates. The arrows 155 are shown at the right side of the NKM-KMD plot 142. A plurality of indexes are displayed near the plurality of arrows 155. The plurality of mass candidates can be evaluated through comparison of the positions of the plurality of display element sequences and the positions of the plurality of arrows 155.

In the illustrated example, it is possible to recognize, for example, that three mass candidates corresponding to indexes #11, #12, and #13 may possibly correspond to the mass of the non-primary-chain segment. Further, it is possible to recognize that two mass candidates corresponding to the indexes #22 and #23 may possibly correspond to the mass of the non-primary-chain segment. When a plurality of mass candidates are determined as hits, one of the mass candidates may be selected as the mass of the non-primary-chain segment in consideration of the total ionic strength. Alternatively, in consideration of the possibility that the derivatization was not performed 100%, a mass candidate corresponding to the largest degree of polymerization may be selected as the mass of the non-primary-chain segment.

For example, when the degree of polymerization determined when all of the repeating units are derivatized is $n_m$, if one of the repeating units is not derivatized, a degree of polymerization, $n_{m-1}$, which is smaller by 1, is determined as the degree of polymerization. Therefore, when a plurality of mass candidates are determined as hits, a mass candidate corresponding to the largest degree of polymerization may be selected.

The RKM-KMD plot 144 includes a plurality of display element groups. In reality, the RKM-KMD plot 144 may include a larger number of the display element groups, but FIG. 12 only shows primary display element groups. The second reference image 156 includes a plurality of circles 160-170 corresponding to the plurality of mass candidates. A plurality of circles 160, 162, and 164 are produced based on the first mass candidate list, and a plurality of circles 166, 168, and 170 are produced based on the second mass candidate list. An index is displayed near each of the circles 160-170.

The plurality of mass candidates may be evaluated through comparison of positions of the plurality of display element groups and positions of the plurality of circles 160-170. Each of the three circles 160, 162, and 164 includes a display element group. In such a case, similar to the above, one of the mass candidates may be selected as the mass of the non-primary-chain segment in consideration of the total ionic strength. Alternatively, a mass candidate corresponding to the largest degree of polymerization may be selected as the mass of the non-primary-chain segment. Of the three circles 166, 168, and 170, each of the circles 168 and 170 includes a display element group. In this case also, similar to the above, one of the mass candidates may be selected as the mass of the non-primary-chain segment in consideration of the total ionic strength, or a mass candidate corresponding to the largest degree of polymerization may be selected as the mass of the non-primary-chain segment.

Figure 13:
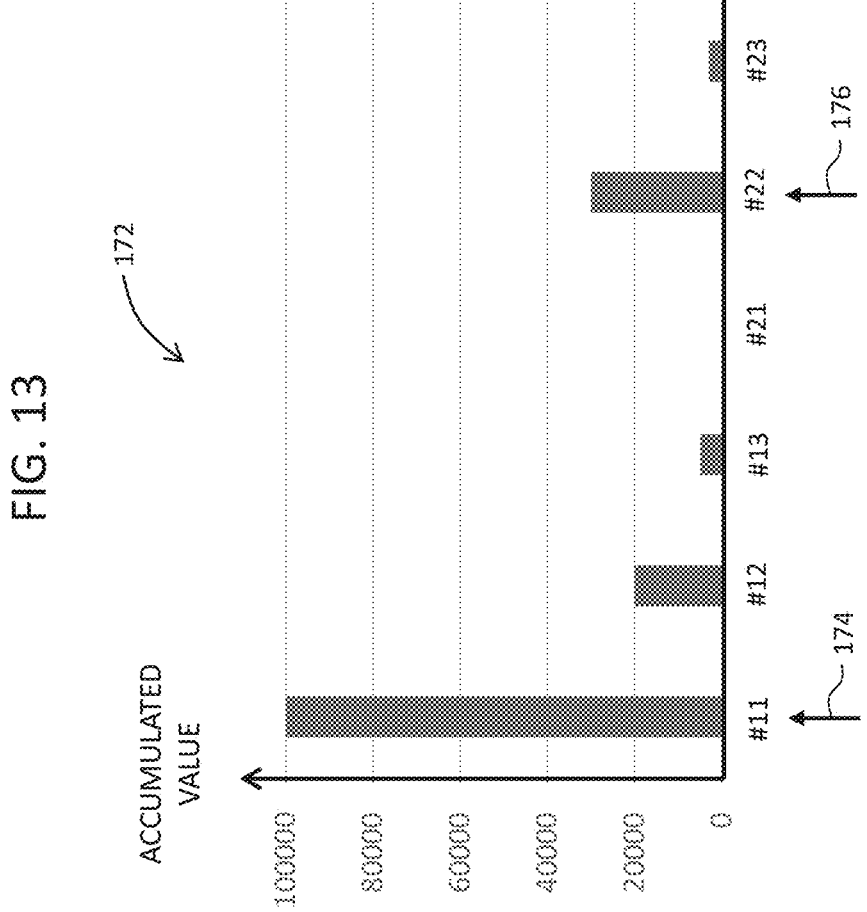
FIG. 13 is a diagram showing a second example of the graph.

FIG. 13 shows another example of the graph. For example, for each circle in the RKM-KMD plot 144 shown in FIG. 12, a peak series belonging thereto is identified, and a total area of the peak series is calculated. Based on a plurality of total peak areas acquired from the plurality of peak series, a graph 172 shown in FIG. 13 is created. On the graph 172, the user may designate a particular index for each polymer (refer to reference numerals 174, 176). In other words, the mass of the non-primary-chain segment may be selected for each polymer.

Figure 14:
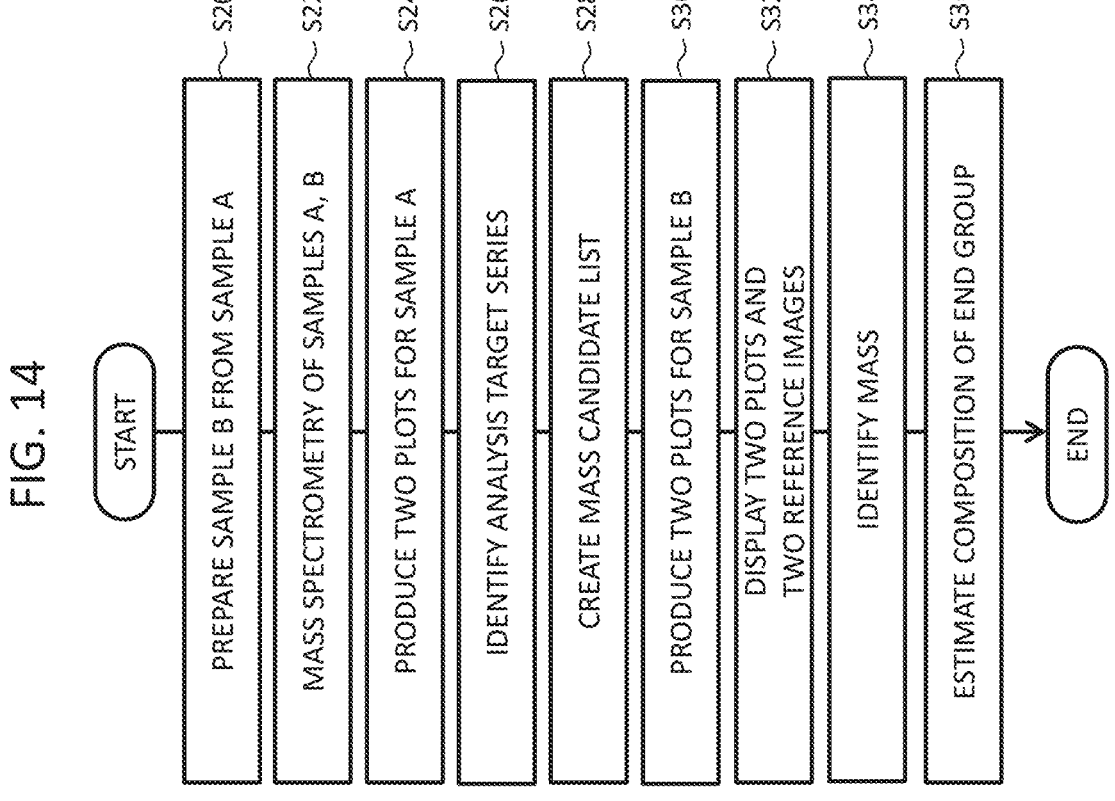
FIG. 14 is a flowchart showing a method of analyzing a polymer according to an embodiment of the present disclosure.

FIG. 14 shows a method of analyzing a polymer according to an embodiment of the present disclosure as a flowchart. In S20, the sample B is prepared through derivatization of the sample A. In S22, the mass spectrometry is executed for each of the sample A and B. With this process, the mass spectrum of the sample A and the mass spectrum of the sample B are produced.

In S24, the NKM-KMD plot and the RKM-KMD plot are produced based on the result of the KMD analysis on the mass spectrum of the sample A. In S26, the analysis target is designated on the NKM-KMD plot and the RKM-KMD plot. That is, a particular peak series included in the mass spectrum of the sample A is designated. In S28, the mass candidate list is created based on the particular peak series. The first reference image and the second reference image are produced based on the result of the KMD analysis on the mass candidate list.

Meanwhile, in S30, the NKM-KMD plot and the RKM-KMD plot are produced based on the result of the KMD analysis on the mass spectrum of the sample B. In S32, the NKM-KMD plot and the first reference image are displayed, and the RKM-KMD plot and the second reference image are displayed. In S34, the mass of the non-primary-chain segment is identified through comparison of the NKM-KMD plot and the first reference image and comparison of the RKM-KMD plot and the second reference image. In S36, the mass of the end group is identified based on the mass of the non-primary-chain segment, and the composition of the end group is analyzed from the mass of the end group.

Alternatively, S30 described above may be executed prior to S24—S28 described above. Alternatively, in S28, the mass candidate list may be created from the mass spectrum of the sample B, and, in S30, the NKM-KMD plot and the RKM-KMD plot may be produced from the mass spectrum of the sample A.

The invention claimed is:

1. A polymer analysis apparatus comprising:
at least one processor configured to:
perform mass spectrometry on a first polymer and a second polymer to acquire a first mass spectrum of the first polymer and a second mass spectrum of the second polymer;
process the first mass spectrum of the first polymer and the second mass spectrum of the second polymer, wherein the second polymer comprises a non-primary-chain segment which is identical to a non-primary-chain segment of the first polymer and a primary-chain segment that is different than a primary-chain segment of the first polymer;
calculate at least one mass candidate for the non-primary-chain segment based on a first polymer molecule mass and a first repeating unit mass identified from the first mass spectrum by repeating subtraction of the first repeating unit mass from the first polymer molecule mass;
apply Kendrick Mass Defect (KMD) analysis on the at least one mass candidate using the first repeating unit mass to produce a first KMD analysis result;
apply KMD analysis on the second mass spectrum using a second repeating unit mass identified from the second mass spectrum to produce a second KMD analysis result; and
produce an image for identifying a mass of the non-primary-chain segment based on the first KMD analysis result and the second KMD analysis result.

2. The polymer analysis apparatus according to claim 1, wherein
the at least one processor is further configured to:
produce a plot representing the second KMD analysis result; and
produce a reference image representing the first KMD analysis result, which is to be added to the plot.

3. The polymer analysis apparatus according to claim 2, wherein
the plot includes at least one of an NKM-KMD plot having a Nominal Kendrick Mass (NKM) axis and a KMD axis, or an RKM-KMD plot having a Remainder of Kendrick Mass (RKM) axis and the KMD axis.

4. The polymer analysis apparatus according to claim 3, wherein
the at least one processor is further configured to calculate a plurality of mass candidates for the non-primary-chain segment, and
the reference image includes at least one of a first reference image including a plurality of figures representing a plurality of KMDs calculated from the plurality of mass candidates and displayed on the NKM-KMD plot, or a second reference image including a plurality of figures representing a plurality of sets of RKM-KMDs calculated from the plurality of mass candidates and displayed on the RKM-KMD plot.

5. The polymer analysis apparatus according to claim 1, wherein
the at least one processor is further configured to: determine, when a remaining mass after subtraction belongs in a mass range which is designated, the remaining mass as a mass candidate.

6. The polymer analysis apparatus according to claim 1, wherein
the at least one processor is further configured to: repeat calculation of a degree of polymerization along with repetition of the subtraction, to thereby create a list in which the plurality of mass candidates and a plurality of degrees of polymerization corresponding thereto are registered.

7. The polymer analysis apparatus according to claim 1, wherein
the at least one processor is further configured to: calculate a total ionic strength for each calculated KMD based on the second mass spectrum, to thereby create a graph representing a plurality of total ionic strengths corresponding to a plurality of KMDs.

8. The polymer analysis apparatus according to claim 1, wherein
one of the first polymer and the second polymer is a polymer before derivatization, and
the other of the first polymer and the second polymer is a polymer after derivatization.

9. A computer-implemented method of analyzing a polymer, comprising:
performing mass spectrometry on a first polymer and a second polymer to acquire a first mass spectrum of the first polymer and a second mass spectrum of the second polymer;
calculating, based on a first polymer molecule mass and a first repeating unit mass identified from the first mass spectrum of the first polymer, at least one mass candidate for a non-primary-chain segment of the first polymer by repeating subtraction of the first repeating unit mass from the first polymer molecule mass;
applying Kendrick Mass Defect (KMD) analysis on the at least one mass candidate using the first repeating unit mass to produce a first KMD analysis result;
applying KMD analysis on the second mass spectrum of the second polymer having a non-primary-chain segment which is identical to the non-primary-chain segment of the first polymer, using a second repeating unit mass identified from the second mass spectrum to produce a second KMD analysis result; and producing an image for identifying a mass of the non-primary-chain segment based on the first KMD analysis result and the second KMD analysis result.

10. The method of analyzing polymer according to claim 9, further comprising:

derivatizing one of the first polymer and the second polymer, so as to prepare the other of the first polymer and the second polymer.

11. A non-transitory recording medium storing a program for executing polymer analysis in an information processing device, the program, when executed, causing the information processing device to perform functions to:

receive a first mass spectrum of a first polymer and a second mass spectrum of a second polymer, wherein the first mass spectrum and the second mass spectrum are acquired by performing mass spectrometry on the first polymer and the second polymer;

calculate, based on a first polymer molecule mass and a first repeating unit mass identified from the first mass spectrum of the first polymer, at least one mass candidate for a non-primary-chain segment of the first polymer by repeating subtraction of the first repeating unit mass from the first polymer molecule mass;

apply Kendrick Mass Defect (KMD) analysis on the at least one mass candidate using the first repeating unit mass to produce a first KMD analysis result;

apply KMD analysis on the second mass spectrum of the second polymer having a non-primary-chain segment which is identical to the non-primary-chain segment of the first polymer, using a second repeating unit mass identified from the second mass spectrum to produce a second KMD analysis result; and produce an image for identifying a mass of the non-primary-chain segment based on the first KMD analysis result and the second KMD analysis result.

* * * * *